(12) United States Patent
Owens et al.

(10) Patent No.: US 8,889,211 B2
(45) Date of Patent: Nov. 18, 2014

(54) COATING PROCESS FOR DRUG DELIVERY BALLOONS USING HEAT-INDUCED REWRAP MEMORY

(75) Inventors: Michael Sean Owens, Victoria, MN (US); Michael Swee, St. Michael, MN (US); Dennis Larson, Maple Grove, MN (US); Stacie Blaskowsi, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 426 days.

(21) Appl. No.: 13/225,166

(22) Filed: Sep. 2, 2011

(65) Prior Publication Data

US 2012/0059316 A1 Mar. 8, 2012

Related U.S. Application Data

(60) Provisional application No. 61/379,608, filed on Sep. 2, 2010.

(51) Int. Cl.
*A61L 33/00* (2006.01)
*A61L 29/16* (2006.01)

(52) U.S. Cl.
CPC ........... *A61L 29/16* (2013.01); *A61L 2300/416* (2013.01); *A61L 2300/45* (2013.01); *A61L 2420/02* (2013.01)
USPC ............. 427/2.1; 424/9.3; 424/423; 424/422; 427/2.24

(58) Field of Classification Search
USPC ......... 424/1.61, 9.3, 400, 9.44, 9.5, 484, 490, 424/423, 448, 422; 604/103; 427/2.24; 264/532
See application file for complete search history.

(56) References Cited

U.S. PATENT DOCUMENTS 304,121 A 8/1884 Munch
4,026,296 A 5/1977 Stoy
(Continued)

FOREIGN PATENT DOCUMENTS

CA 2363119 8/2000
DE 19908318 8/2000
(Continued)

OTHER PUBLICATIONS

Mondesire (Targeting Mammalian Target of Rapamycin Synergistically Enhances Chemotherapy-Induced Cytotoxicity in Breast Cancer Cells, 10 Clin. Cancer Res. 7031 (2004).

(Continued)

*Primary Examiner* — Dah-Wei D Yuan
*Assistant Examiner* — Andrew Bowman
(74) *Attorney, Agent, or Firm* — Vidas, Arrett & Steinkraus, P.A.

(57) ABSTRACT

A method of producing a drug coated balloon that comprises the steps of: subjecting a balloon catheter with a folded and wrapped balloon thereon to a pre-annealing step to induce a fold/wrap memory in the resulting pre-annealed balloon; unfolding the pre-annealed balloon sufficiently to expose the full circumferential surface of the balloon by application of an inflation pressure that retains said fold/wrap memory; applying a drug coating formulation to the unfolded balloon surface; releasing pressure to relax the balloon and induce creasing along fold memory; and evacuating the balloon slowly to induce refolding and rewrapping of the balloon. The method overcomes the need to use a folding apparatus to fold and wrap a drug coated balloon.

15 Claims, 1 Drawing Sheet

(56) References Cited

U.S. PATENT DOCUMENTS

| | | |
|---|---|---|
| 4,186,745 A | 2/1980 | Lewis |
| 4,364,392 A | 12/1982 | Strother |
| 4,481,323 A | 11/1984 | Sterling |
| 4,490,421 A | 12/1984 | Levy |
| 4,515,593 A | 5/1985 | Norton |
| 4,589,873 A | 5/1986 | Schwartz |
| 4,603,152 A | 7/1986 | Laurin |
| 4,610,688 A | 9/1986 | Silvestrini |
| 4,644,936 A | 2/1987 | Schiff |
| 4,693,243 A | 9/1987 | Buras |
| 4,759,758 A | 7/1988 | Gabbay |
| 4,769,013 A | 9/1988 | Lorenz |
| 4,784,647 A | 11/1988 | Gross |
| 4,800,882 A | 1/1989 | Gianturco |
| 4,886,062 A | 12/1989 | Wiktor |
| 4,906,244 A | 3/1990 | Pinchuk et al. |
| 4,931,583 A | 6/1990 | Hull |
| 4,950,239 A | 8/1990 | Gahara |
| 4,950,256 A | 8/1990 | Luther |
| 4,994,033 A | 2/1991 | Shockey |
| 5,026,607 A | 6/1991 | Kiezulas |
| 5,027,996 A | 7/1991 | Fefeu |
| 5,041,100 A | 8/1991 | Rowland |
| 5,049,131 A | 9/1991 | Deuss |
| 5,087,244 A | 2/1992 | Wolinsky |
| 5,091,205 A | 2/1992 | Fan |
| 2,098,381 A | 3/1992 | Schneider |
| 5,092,841 A | 3/1992 | Spears |
| 5,098,381 A | 3/1992 | Schneider |
| 5,102,402 A | 4/1992 | Dror |
| 5,135,516 A | 8/1992 | Sahatjian |
| 5,169,933 A | 12/1992 | Anderson |
| 5,180,366 A | 1/1993 | Woods |
| 5,199,951 A | 4/1993 | Spears |
| 5,213,576 A | 5/1993 | Abiuso |
| 5,213,580 A | 5/1993 | Slepian |
| 5,232,444 A | 8/1993 | Just |
| 5,236,413 A | 8/1993 | Feiring |
| 5,250,069 A | 10/1993 | Nobuyoshi |
| 5,264,260 A | 11/1993 | Saab |
| 5,270,086 A | 12/1993 | Hamlin |
| 5,282,785 A | 2/1994 | Shapland |
| 5,286,254 A | 2/1994 | Shapland |
| 5,295,962 A | 3/1994 | Crocker |
| 5,304,121 A | 4/1994 | Sahatjian |
| 5,318,531 A | 6/1994 | Leone |
| 5,320,634 A | 6/1994 | Vigil |
| 5,324,261 A | 6/1994 | Amundson |
| 5,328,468 A | 7/1994 | Kaneko |
| 5,328,471 A | 7/1994 | Slepian |
| 5,342,307 A * | 8/1994 | Euteneuer et al. ............ 604/103 |
| 5,342,628 A | 8/1994 | Picha |
| 5,344,400 A | 9/1994 | Kaneko |
| 5,344,402 A | 9/1994 | Crocker |
| 5,362,831 A | 11/1994 | Mongelli |
| 5,368,566 A | 11/1994 | Crocker |
| 5,370,614 A | 12/1994 | Amundson |
| 5,380,299 A | 1/1995 | Fearnot |
| 5,383,928 A | 1/1995 | Scott |
| 5,385,152 A | 1/1995 | Abele |
| 5,405,472 A | 4/1995 | Leone |
| 5,419,760 A | 5/1995 | Narciso |
| 5,421,826 A | 6/1995 | Crocker |
| 5,425,703 A | 6/1995 | Feiring |
| 5,427,767 A | 6/1995 | Kresse |
| 5,439,446 A | 8/1995 | Barry |
| 5,443,496 A | 8/1995 | Schwartz |
| 5,447,724 A | 9/1995 | Helmus |
| 5,449,382 A | 9/1995 | Dayton |
| 5,464,650 A | 11/1995 | Berg |
| 5,470,307 A | 11/1995 | Lindall |
| 5,489,525 A | 2/1996 | Pastan |
| 5,498,238 A | 3/1996 | Shapland |
| 5,499,971 A | 3/1996 | Shapland |
| 5,500,180 A | 3/1996 | Anderson |
| 5,542,926 A | 8/1996 | Crocker |
| 5,545,208 A | 8/1996 | Wolff |
| 5,549,603 A | 8/1996 | Feiring |
| 5,554,119 A | 9/1996 | Harrison |
| 5,554,182 A | 9/1996 | Dinh |
| 5,556,383 A | 9/1996 | Wang et al. |
| 5,558,642 A | 9/1996 | Schweich, Jr. |
| 5,562,922 A | 10/1996 | Lambert |
| 5,569,184 A | 10/1996 | Crocker |
| 5,569,463 A | 10/1996 | Helmus |
| 5,571,089 A | 11/1996 | Crocker |
| 5,578,075 A | 11/1996 | Dayton |
| 5,588,962 A | 12/1996 | Nicholas |
| 5,599,306 A | 2/1997 | Klein |
| 5,599,307 A | 2/1997 | Bacher |
| 5,609,629 A | 3/1997 | Fearnot |
| 5,611,775 A | 3/1997 | Machold |
| 5,616,149 A | 4/1997 | Barath |
| 5,624,411 A | 4/1997 | Tuch |
| 5,626,862 A | 5/1997 | Brem |
| 5,628,730 A | 5/1997 | Shapland |
| 5,629,008 A | 5/1997 | Lee |
| 5,634,901 A | 6/1997 | Alba |
| 5,637,086 A | 6/1997 | Ferguson |
| 5,651,986 A | 7/1997 | Brem |
| 5,665,772 A | 9/1997 | Cottens |
| 5,669,874 A | 9/1997 | Feiring |
| 5,674,192 A | 10/1997 | Sahatjian |
| 5,674,241 A | 10/1997 | Bley |
| 5,679,400 A | 10/1997 | Tuch |
| 5,681,522 A * | 10/1997 | Roychowdhury ............ 264/532 |
| 5,685,847 A | 11/1997 | Barry |
| 5,688,516 A | 11/1997 | Raad |
| 5,693,034 A | 12/1997 | Buscemi |
| 5,697,967 A | 12/1997 | Dinh |
| 5,704,908 A | 1/1998 | Hofmann |
| 5,707,385 A | 1/1998 | Williams |
| 5,716,981 A | 2/1998 | Hunter |
| 5,728,066 A | 3/1998 | Daneshvar |
| 5,733,925 A | 3/1998 | Kunz |
| 5,766,158 A | 6/1998 | Opolski |
| 5,769,883 A | 6/1998 | Buscemi et al. |
| 5,797,877 A | 8/1998 | Hamilton |
| 5,800,538 A | 9/1998 | Slepian |
| 5,807,306 A | 9/1998 | Shapland |
| 5,810,763 A | 9/1998 | Feiring |
| 5,833,657 A | 11/1998 | Reinhardt et al. |
| 5,833,658 A | 11/1998 | Levy |
| 5,843,089 A | 12/1998 | Sahatjian |
| 5,854,382 A | 12/1998 | Loomis |
| 5,855,546 A | 1/1999 | Hastings |
| 5,857,998 A | 1/1999 | Barry |
| 5,865,801 A | 2/1999 | Houser |
| 5,868,719 A | 2/1999 | Tsukernik |
| 5,869,127 A | 2/1999 | Zhong |
| 5,876,374 A | 3/1999 | Alba |
| 5,893,840 A | 4/1999 | Hull |
| 5,900,246 A | 5/1999 | Lambert |
| 5,902,266 A | 5/1999 | Leone |
| 5,902,299 A | 5/1999 | Jayaraman |
| 5,928,279 A | 7/1999 | Shannon |
| 5,935,275 A | 8/1999 | Burgard |
| 5,935,506 A | 8/1999 | Schmitz |
| 5,947,977 A | 9/1999 | Slepian |
| 5,954,693 A | 9/1999 | Barry |
| 5,954,706 A | 9/1999 | Sahatjian |
| 5,977,163 A | 11/1999 | Li |
| 5,981,568 A | 11/1999 | Kunz |
| 6,048,356 A | 4/2000 | Ravenscroft |
| 6,048,515 A | 4/2000 | Kresse |
| 6,048,620 A | 4/2000 | Zhong |
| 6,099,454 A | 8/2000 | Hastings |
| 6,099,926 A | 8/2000 | Thakrar |
| 6,129,705 A | 10/2000 | Grantz |
| 6,142,973 A | 11/2000 | Carleton |
| 6,146,356 A | 11/2000 | Wang et al. |
| 6,146,358 A | 11/2000 | Rowe |
| 6,183,658 B1 | 2/2001 | Lesniak |
| 6,186,745 B1 | 2/2001 | Johnson |

(56) References Cited

U.S. PATENT DOCUMENTS

| | | |
|---|---|---|
| 6,195,583 B1 | 2/2001 | Feiring |
| 6,203,551 B1 | 3/2001 | Wu |
| 6,218,016 B1 | 4/2001 | Tedeschi |
| 6,219,577 B1 | 4/2001 | Brown |
| 6,240,407 B1 | 5/2001 | Chang |
| 6,245,103 B1 | 6/2001 | Stinson |
| 6,262,107 B1 | 7/2001 | Li |
| 6,270,522 B1 | 8/2001 | Simhambhatla |
| 6,280,411 B1 | 8/2001 | Lennox |
| 6,283,947 B1 | 9/2001 | Mirzaee |
| 6,287,332 B1 | 9/2001 | Bolz |
| 6,296,619 B1 | 10/2001 | Brisken |
| 6,299,604 B1 | 10/2001 | Ragheb |
| 6,306,166 B1 | 10/2001 | Barry |
| 6,344,028 B1 | 2/2002 | Barry |
| 6,355,029 B1 | 3/2002 | Joye |
| 6,364,856 B1 | 4/2002 | Ding |
| 6,364,893 B1 | 4/2002 | Sahatjian |
| 6,369,039 B1 | 4/2002 | Palasis |
| 6,389,314 B2 | 5/2002 | Feiring |
| 6,391,033 B2 | 5/2002 | Ryan |
| 6,398,708 B1 | 6/2002 | Hastings |
| 6,409,716 B1 | 6/2002 | Sahatjian |
| 6,418,448 B1 | 7/2002 | Sarkar |
| 6,419,692 B1 | 7/2002 | Yang |
| 6,428,534 B1 | 8/2002 | Joye |
| 6,432,102 B2 | 8/2002 | Joye |
| 6,440,990 B1 | 8/2002 | Cottens |
| 6,443,941 B1 | 9/2002 | Slepian |
| 6,451,373 B1 | 9/2002 | Hossainy |
| 6,468,297 B1 | 10/2002 | Williams |
| 6,494,862 B1 | 12/2002 | Ray |
| 6,506,408 B1 | 1/2003 | Palasis |
| 6,511,477 B2 | 1/2003 | Altman |
| 6,514,245 B1 | 2/2003 | Williams |
| 6,517,533 B1 | 2/2003 | Swaminathan |
| 6,524,274 B1 | 2/2003 | Rosenthal |
| 6,527,740 B1 | 3/2003 | Jackson |
| 6,537,194 B1 | 3/2003 | Winkler |
| 6,541,039 B1 | 4/2003 | Lesniak |
| 6,544,221 B1 | 4/2003 | Kokish |
| 6,544,223 B1 | 4/2003 | Kokish |
| 6,545,097 B2 | 4/2003 | Pinchuk |
| 6,548,569 B1 | 4/2003 | Williams |
| 6,582,353 B1 | 6/2003 | Hastings |
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien |
| 6,623,749 B2 | 9/2003 | Williams |
| 6,638,246 B1 | 10/2003 | Naimark |
| 6,645,135 B1 | 11/2003 | Bhat |
| 6,648,879 B2 | 11/2003 | Joye et al. |
| 6,656,156 B2 | 12/2003 | Yang |
| 6,663,880 B1 | 12/2003 | Roorda |
| 6,682,545 B1 | 1/2004 | Kester |
| 6,685,648 B2 | 2/2004 | Flaherty |
| 6,699,272 B2 | 3/2004 | Slepian |
| 6,706,013 B1 | 3/2004 | Bhat |
| 6,730,105 B2 | 5/2004 | Shiber |
| 6,733,474 B2 | 5/2004 | Kusleika |
| 6,780,324 B2 | 8/2004 | Le Garrec |
| 6,783,543 B2 | 8/2004 | Jang |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta |
| 6,805,898 B1 | 10/2004 | Wu |
| 6,811,550 B2 | 11/2004 | Holland |
| 6,838,493 B2 | 1/2005 | Williams |
| 6,858,644 B2 | 2/2005 | Benigni |
| 6,863,861 B1 | 3/2005 | Zhang |
| 6,867,247 B2 | 3/2005 | Williams |
| 6,890,339 B2 | 5/2005 | Sahatjian |
| 6,890,583 B2 | 5/2005 | Chudzik |
| 6,899,731 B2 | 5/2005 | Li |
| 6,908,462 B2 | 6/2005 | Joye |
| 6,918,927 B2 | 7/2005 | Bates |
| 6,923,996 B2 | 8/2005 | Epstein |
| 6,939,320 B2 | 9/2005 | Lennox |
| 6,942,680 B2 | 9/2005 | Grayzel |
| 6,955,661 B1 | 10/2005 | Herweck |
| 6,960,346 B2 | 11/2005 | Shukla |
| 6,972,015 B2 | 12/2005 | Joye |
| 6,991,647 B2 | 1/2006 | Jadhav |
| 7,005,414 B2 | 2/2006 | Barnikol |
| 7,008,979 B2 | 3/2006 | Schottman |
| 7,018,371 B2 | 3/2006 | Forman |
| 7,037,319 B2 | 5/2006 | Weber |
| 7,048,714 B2 | 5/2006 | Richter |
| 7,056,533 B2 | 6/2006 | Chudzik |
| 7,060,051 B2 | 6/2006 | Palasis |
| 7,060,062 B2 | 6/2006 | Joye |
| 7,066,904 B2 | 6/2006 | Rosenthal |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | McHale |
| 7,166,098 B1 | 1/2007 | Steward |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford |
| 7,323,189 B2 | 1/2008 | Pathak |
| 7,335,184 B2 | 2/2008 | Laguna |
| 7,357,940 B2 | 4/2008 | Richard |
| 7,364,585 B2 | 4/2008 | Weber |
| 7,371,257 B2 | 5/2008 | Sahatjian |
| 7,381,418 B2 | 6/2008 | Richard |
| 7,393,685 B1 | 7/2008 | Jordan |
| 7,402,172 B2 | 7/2008 | Chin |
| 7,407,671 B2 | 8/2008 | Mcbride |
| 7,407,684 B2 | 8/2008 | Spencer |
| 7,459,169 B2 | 12/2008 | Nilsson |
| 7,462,165 B2 | 12/2008 | Ding |
| 7,470,252 B2 | 12/2008 | Mickley |
| 7,473,242 B2 | 1/2009 | Donovan |
| 7,491,188 B2 | 2/2009 | Holman |
| 7,494,497 B2 | 2/2009 | Weber |
| 7,527,604 B2 | 5/2009 | Naimark |
| 7,553,292 B2 | 6/2009 | Kilpatrick |
| 7,563,324 B1 | 7/2009 | Chen |
| 7,572,245 B2 | 8/2009 | Herweck |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze |
| 7,718,213 B1 | 5/2010 | Scheer |
| 7,731,685 B2 | 6/2010 | Ragheb |
| 7,744,644 B2 | 6/2010 | Weber |
| 7,750,041 B2 | 7/2010 | Speck |
| 7,753,876 B2 | 7/2010 | Cervantes |
| 7,758,892 B1 | 7/2010 | Chen |
| 7,762,995 B2 | 7/2010 | Eversull |
| 7,767,219 B2 | 8/2010 | Weber |
| 7,771,740 B2 | 8/2010 | Strickler |
| 7,773,447 B2 | 8/2010 | Kajigaya |
| 7,794,751 B2 | 9/2010 | Chudzik |
| 7,803,149 B2 | 9/2010 | Bates |
| 7,811,622 B2 | 10/2010 | Bates |
| 8,291,854 B2 | 10/2012 | Behnisch |
| 2001/0020151 A1 | 9/2001 | Reed |
| 2002/0010489 A1 | 1/2002 | Grayzel |
| 2002/0037358 A1 | 3/2002 | Barry |
| 2002/0041898 A1 | 4/2002 | Unger |
| 2002/0042645 A1 | 4/2002 | Shannon |

(56) References Cited

U.S. PATENT DOCUMENTS

| | | |
|---|---|---|
| 2002/0151844 A1 | 10/2002 | Yang |
| 2002/0183581 A1 | 12/2002 | Yoe |
| 2003/0028210 A1 | 2/2003 | Boyle |
| 2003/0040712 A1 | 2/2003 | Ray |
| 2003/0060877 A1 | 3/2003 | Falotico |
| 2003/0064965 A1 | 4/2003 | Richter |
| 2003/0077253 A1 | 4/2003 | Palasis |
| 2003/0083740 A1 | 5/2003 | Pathak |
| 2003/0114791 A1 | 6/2003 | Rosenthal |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz |
| 2003/0236514 A1 | 12/2003 | Schwarz |
| 2004/0023851 A1 | 2/2004 | Barnikol |
| 2004/0033251 A1 | 2/2004 | Sparer |
| 2004/0034336 A1 | 2/2004 | Scott |
| 2004/0039437 A1 | 2/2004 | Sparer |
| 2004/0044308 A1 | 3/2004 | Naimark |
| 2004/0044404 A1 | 3/2004 | Stucke |
| 2004/0047911 A1 | 3/2004 | Lyu |
| 2004/0059290 A1 | 3/2004 | Palasis |
| 2004/0064093 A1 | 4/2004 | Hektner |
| 2004/0073284 A1 | 4/2004 | Bates |
| 2004/0077948 A1 | 4/2004 | Violante |
| 2004/0086569 A1 | 5/2004 | Sparer |
| 2004/0098014 A1 | 5/2004 | Flugelman |
| 2004/0098108 A1 | 5/2004 | Harder |
| 2004/0111144 A1 | 6/2004 | Lawin |
| 2004/0115273 A1 | 6/2004 | Sparer |
| 2004/0117222 A1 | 6/2004 | Rokosz |
| 2004/0127978 A1 | 7/2004 | Sparer |
| 2004/0137066 A1 | 7/2004 | Jayaraman |
| 2004/0142011 A1 | 7/2004 | Nilsson |
| 2004/0143287 A1 | 7/2004 | Konstantino |
| 2004/0175406 A1 | 9/2004 | Schwarz |
| 2004/0180039 A1 | 9/2004 | Toner |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett |
| 2004/0224003 A1 | 11/2004 | Schultz |
| 2004/0224080 A1 | 11/2004 | Epstein |
| 2004/0230176 A1 | 11/2004 | Shanahan |
| 2004/0234575 A1 | 11/2004 | Horres |
| 2004/0260239 A1 | 12/2004 | Kusleika |
| 2005/0015046 A1 | 1/2005 | Weber |
| 2005/0025801 A1 | 2/2005 | Richard |
| 2005/0025802 A1 | 2/2005 | Richard |
| 2005/0025803 A1 | 2/2005 | Richard |
| 2005/0025848 A1 | 2/2005 | Huang |
| 2005/0027283 A1 | 2/2005 | Richard |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco |
| 2005/0060028 A1 | 3/2005 | Horres |
| 2005/0064005 A1 | 3/2005 | Dinh |
| 2005/0064038 A1 | 3/2005 | Dinh |
| 2005/0101522 A1 | 5/2005 | Speck |
| 2005/0106206 A1 | 5/2005 | Herweck |
| 2005/0129727 A1 | 6/2005 | Weber |
| 2005/0129731 A1 | 6/2005 | Horres |
| 2005/0137618 A1 | 6/2005 | Kunis |
| 2005/0154416 A1 | 7/2005 | Herweck |
| 2005/0158359 A1 | 7/2005 | Epstein |
| 2005/0169969 A1 | 8/2005 | Li |
| 2005/0176678 A1 | 8/2005 | Horres |
| 2005/0181015 A1 | 8/2005 | Zhong |
| 2005/0182361 A1 | 8/2005 | Lennox |
| 2005/0209548 A1 | 9/2005 | Dev |
| 2005/0215722 A1 | 9/2005 | Pinchunk |
| 2005/0220853 A1 | 10/2005 | Dao |
| 2005/0222677 A1 | 10/2005 | Bates |
| 2005/0226991 A1 | 10/2005 | Hossainy |
| 2005/0233061 A1 | 10/2005 | Schwarz |
| 2005/0244456 A1 | 11/2005 | Nilsson |
| 2005/0244459 A1 | 11/2005 | Dewitt |
| 2005/0246009 A1 | 11/2005 | Toner |
| 2005/0251106 A1 | 11/2005 | Cervantes |
| 2005/0273049 A1 | 12/2005 | Krulevitch |
| 2005/0273075 A1 | 12/2005 | Krulevitch |
| 2005/0278021 A1 | 12/2005 | Bates |
| 2005/0288629 A1 | 12/2005 | Kunis |
| 2006/0002968 A1 | 1/2006 | Stewart |
| 2006/0002973 A1* | 1/2006 | Barry et al. .................. 424/423 |
| 2006/0013853 A1 | 1/2006 | Richard |
| 2006/0013854 A1 | 1/2006 | Strickler |
| 2006/0020243 A1 | 1/2006 | Speck |
| 2006/0020331 A1 | 1/2006 | Bates |
| 2006/0025848 A1 | 2/2006 | Weber |
| 2006/0041225 A1 | 2/2006 | Wallace |
| 2006/0057208 A1 | 3/2006 | Holzer |
| 2006/0058815 A1 | 3/2006 | Mickley |
| 2006/0067977 A1 | 3/2006 | Labrecque |
| 2006/0079836 A1 | 4/2006 | Holman |
| 2006/0083768 A1 | 4/2006 | Labrecque |
| 2006/0085058 A1 | 4/2006 | Rosenthal |
| 2006/0088596 A1 | 4/2006 | Labrecque |
| 2006/0112536 A1 | 6/2006 | Herweck |
| 2006/0121081 A1 | 6/2006 | Labrecque |
| 2006/0121088 A1 | 6/2006 | Hunter |
| 2006/0129093 A1 | 6/2006 | Jackson |
| 2006/0134160 A1 | 6/2006 | Troczynski |
| 2006/0134168 A1 | 6/2006 | Chappa |
| 2006/0135548 A1 | 6/2006 | Keri |
| 2006/0147491 A1 | 7/2006 | Dewitt |
| 2006/0165754 A1 | 7/2006 | Ranade |
| 2006/0167407 A1 | 7/2006 | Weber |
| 2006/0171982 A1 | 8/2006 | Timm |
| 2006/0171984 A1 | 8/2006 | Cromack |
| 2006/0171985 A1 | 8/2006 | Richard |
| 2006/0184112 A1 | 8/2006 | Horn |
| 2006/0190022 A1 | 8/2006 | Beyar |
| 2006/0193890 A1 | 8/2006 | Owens |
| 2006/0193891 A1 | 8/2006 | Richard |
| 2006/0195176 A1 | 8/2006 | Bates |
| 2006/0200048 A1 | 9/2006 | Furst |
| 2006/0200556 A1 | 9/2006 | Brave |
| 2006/0204537 A1 | 9/2006 | Ratner |
| 2006/0212106 A1 | 9/2006 | Weber |
| 2006/0224115 A1 | 10/2006 | Willard |
| 2006/0228452 A1 | 10/2006 | Cromack |
| 2006/0240070 A1 | 10/2006 | Cromack |
| 2006/0280858 A1 | 12/2006 | Kokish |
| 2006/0286071 A1 | 12/2006 | Epstein |
| 2006/0286141 A1 | 12/2006 | Campbell |
| 2007/0003599 A1 | 1/2007 | Schwarz |
| 2007/0020307 A1 | 1/2007 | Zhong |
| 2007/0027523 A1 | 2/2007 | Toner |
| 2007/0067882 A1 | 3/2007 | Atanasoska |
| 2007/0078413 A1 | 4/2007 | Stenzel |
| 2007/0083149 A1 | 4/2007 | Steward |
| 2007/0088246 A1 | 4/2007 | Steward |
| 2007/0088255 A1 | 4/2007 | Toner |
| 2007/0093745 A1 | 4/2007 | Steward |
| 2007/0104766 A1 | 5/2007 | Wang |
| 2007/0106250 A1 | 5/2007 | Seward |
| 2007/0106363 A1 | 5/2007 | Weber |
| 2007/0112330 A1 | 5/2007 | Palasis |
| 2007/0129474 A1 | 6/2007 | Salamone |
| 2007/0129792 A1 | 6/2007 | Picart |
| 2007/0150465 A1 | 6/2007 | Brave |
| 2007/0150466 A1 | 6/2007 | Brave |
| 2007/0150470 A1 | 6/2007 | Brave |
| 2007/0150515 A1 | 6/2007 | Brave |
| 2007/0150646 A1 | 6/2007 | Yoon |
| 2007/0154554 A1 | 7/2007 | Burgermeister |
| 2007/0178136 A1 | 8/2007 | Arney |
| 2007/0185561 A1 | 8/2007 | Schmitz |
| 2007/0212386 A1 | 9/2007 | Patravale |
| 2007/0212387 A1 | 9/2007 | Patravale |
| 2007/0212393 A1 | 9/2007 | Patravale |
| 2007/0212394 A1 | 9/2007 | Reyes |

(56) References Cited

U.S. PATENT DOCUMENTS

| | | |
|---|---|---|
| 2007/0224234 A1 | 9/2007 | Steckel |
| 2007/0225800 A1 | 9/2007 | Sahatjian |
| 2007/0232996 A1 | 10/2007 | Andersen |
| 2007/0244548 A1 | 10/2007 | Myers |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2008/0020013 A1 | 1/2008 | Reyes |
| 2008/0021385 A1 | 1/2008 | Barry |
| 2008/0027421 A1 | 1/2008 | Vancelette |
| 2008/0031173 A1 | 2/2008 | Zhang |
| 2008/0040314 A1 | 2/2008 | Brave |
| 2008/0050415 A1 | 2/2008 | Atanasoska |
| 2008/0051541 A1 | 2/2008 | Strickler |
| 2008/0057102 A1 | 3/2008 | Roorda |
| 2008/0071350 A1 | 3/2008 | Stinson |
| 2008/0071358 A1 | 3/2008 | Weber |
| 2008/0089958 A1 | 4/2008 | Diehl |
| 2008/0091008 A1 | 4/2008 | Viswanath |
| 2008/0095847 A1 | 4/2008 | Glauser |
| 2008/0102033 A1 | 5/2008 | Speck |
| 2008/0102034 A1 | 5/2008 | Speck |
| 2008/0104004 A1 | 5/2008 | Brave |
| 2008/0113081 A1 | 5/2008 | Hossainy |
| 2008/0114331 A1 | 5/2008 | Holman |
| 2008/0118544 A1* | 5/2008 | Wang ............................ 424/423 |
| 2008/0132992 A1 | 6/2008 | Bates |
| 2008/0140002 A1 | 6/2008 | Ramzipoor |
| 2008/0145396 A1 | 6/2008 | Bates |
| 2008/0145398 A1 | 6/2008 | Bates |
| 2008/0157444 A1 | 7/2008 | Melsheimer |
| 2008/0171129 A1 | 7/2008 | Ranade |
| 2008/0175887 A1 | 7/2008 | Wang |
| 2008/0195042 A1 | 8/2008 | Weber |
| 2008/0195079 A1 | 8/2008 | Moore |
| 2008/0199506 A1 | 8/2008 | Horres |
| 2008/0206304 A1 | 8/2008 | Lindquist |
| 2008/0208182 A1 | 8/2008 | Lafontaine |
| 2008/0220041 A1 | 9/2008 | Brito |
| 2008/0249464 A1 | 10/2008 | Spencer |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber |
| 2008/0311173 A1 | 12/2008 | Schwarz |
| 2009/0005849 A1 | 1/2009 | Hossainy |
| 2009/0018501 A1 | 1/2009 | Yribarren |
| 2009/0024200 A1 | 1/2009 | Wilcox |
| 2009/0047414 A1 | 2/2009 | Corbeil |
| 2009/0048667 A1 | 2/2009 | Mochizuki |
| 2009/0054837 A1 | 2/2009 | Von Holst |
| 2009/0069883 A1 | 3/2009 | Ding |
| 2009/0076448 A1 | 3/2009 | Consigny |
| 2009/0088735 A1 | 4/2009 | Abboud |
| 2009/0098176 A1 | 4/2009 | Helmus |
| 2009/0105686 A1 | 4/2009 | Snow |
| 2009/0105687 A1 | 4/2009 | Deckman |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates |
| 2009/0187144 A1 | 7/2009 | Jayaraman |
| 2009/0192537 A1 | 7/2009 | Obrien |
| 2009/0204082 A1 | 8/2009 | Wesselmann |
| 2009/0226502 A1 | 9/2009 | Chen |
| 2009/0227948 A1 | 9/2009 | Chen |
| 2009/0227949 A1 | 9/2009 | Knapp |
| 2009/0227980 A1 | 9/2009 | Kangas |
| 2009/0246252 A1 | 10/2009 | Arps |
| 2009/0254063 A1 | 10/2009 | Oepen |
| 2009/0258049 A1 | 10/2009 | Klein |
| 2009/0276036 A1 | 11/2009 | Nagura |
| 2009/0297441 A1* | 12/2009 | Canham et al. ............... 424/1.61 |
| 2009/0299355 A1 | 12/2009 | Bencini |
| 2009/0299356 A1 | 12/2009 | Watson |
| 2009/0318848 A1 | 12/2009 | Shippy, III |
| 2010/0010470 A1 | 1/2010 | Bates |
| 2010/0015200 A1 | 1/2010 | Mcclain |
| 2010/0023108 A1 | 1/2010 | Toner |
| 2010/0030183 A1 | 2/2010 | Toner |
| 2010/0036585 A1 | 2/2010 | Scharfenberg |
| 2010/0049294 A1 | 2/2010 | Zukowski |
| 2010/0049296 A1 | 2/2010 | Sarasam |
| 2010/0049309 A1 | 2/2010 | Bates |
| 2010/0055294 A1 | 3/2010 | Wang |
| 2010/0056985 A1 | 3/2010 | Weber |
| 2010/0063585 A1 | 3/2010 | Hoffmann |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber |
| 2010/0092540 A1 | 4/2010 | Pinchuk |
| 2010/0096781 A1 | 4/2010 | Huang |
| 2010/0125239 A1 | 5/2010 | Perry |
| 2010/0131043 A1 | 5/2010 | Casas |
| 2010/0145266 A1 | 6/2010 | Orlowski |
| 2010/0179475 A1 | 7/2010 | Hoffmann |
| 2010/0198190 A1 | 8/2010 | Michal |
| 2010/0209471 A1 | 8/2010 | Weber |
| 2010/0209473 A1 | 8/2010 | Dhont |
| 2010/0228333 A1 | 9/2010 | Drasler |
| 2010/0233228 A1 | 9/2010 | Speck |
| 2010/0233236 A1 | 9/2010 | Zhao |
| 2010/0239635 A1 | 9/2010 | McClain |
| 2010/0249702 A1 | 9/2010 | Magana |
| 2010/0256748 A1 | 10/2010 | Taylor |
| 2010/0261662 A1 | 10/2010 | Schreck |
| 2010/0268191 A1 | 10/2010 | Trudel |
| 2010/0272773 A1 | 10/2010 | Kangas |
| 2010/0272778 A1 | 10/2010 | McClain |
| 2010/0285085 A1 | 11/2010 | Stankus |
| 2010/0292641 A1 | 11/2010 | Wijay |
| 2010/0298769 A1 | 11/2010 | Schewe |
| 2010/0312182 A1 | 12/2010 | Adden |
| 2010/0318020 A1 | 12/2010 | Atanasoska |
| 2010/0324645 A1 | 12/2010 | Stankus |
| 2010/0324648 A1 | 12/2010 | Scheller |
| 2010/0331816 A1 | 12/2010 | Dadino |
| 2010/0331947 A1 | 12/2010 | Shalev |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas |
| 2011/0054443 A1 | 3/2011 | Weber |
| 2011/0087191 A1 | 4/2011 | Scheuermann |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0190864 A1 | 8/2011 | McClain |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0059316 A1 | 3/2012 | Owens |
| 2012/0095396 A1 | 4/2012 | Radhakrishnan |
| 2012/0231037 A1 | 9/2012 | Levi |
| 2013/0035483 A1 | 2/2013 | Zeng |
| 2013/0053947 A1 | 2/2013 | Kangas |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |

(56) References Cited

FOREIGN PATENT DOCUMENTS

| | | |
|---|---|---|
| EP | 0568310 | 11/1993 |
| EP | 0734721 | 3/1996 |
| EP | 0747069 | 4/1996 |
| EP | 0519063 | 5/1996 |
| EP | 0717041 | 6/1996 |
| EP | 0770401 | 5/1997 |
| EP | 0633796 | 11/1997 |
| EP | 0937469 | 8/1999 |
| EP | 0950386 | 10/1999 |
| EP | 0623354 | 10/2002 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1666071 | 8/2007 |
| EP | 1666070 | 9/2007 |
| EP | 1857127 | 11/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| EP | 2241341 | 1/2011 |
| GB | 2112646 | 7/1983 |
| GB | 2127839 | 9/1983 |
| JP | 663145 | 3/1994 |
| JP | 663145 A | 3/1994 |
| JP | 2002240847 | 8/2002 |
| RU | 200513564 | 4/2004 |
| WO | 8912478 | 12/1989 |
| WO | 9108790 | 6/1991 |
| WO | 9211896 | 7/1992 |
| WO | 9215286 | 9/1992 |
| WO | 9306792 | 4/1993 |
| WO | 9421308 | 9/1994 |
| WO | 9423787 | 10/1994 |
| WO | 9503036 | 2/1995 |
| WO | 9503083 | 2/1995 |
| WO | 9508305 | 3/1995 |
| WO | 9521636 | 8/1995 |
| WO | 9625176 | 8/1996 |
| WO | 9632907 | 10/1996 |
| WO | 9639949 | 12/1996 |
| WO | 9710011 | 3/1997 |
| WO | 9725085 | 7/1997 |
| WO | 9733552 | 9/1997 |
| WO | 9741916 | 11/1997 |
| WO | 9831415 | 7/1998 |
| WO | 9901458 | 1/1999 |
| WO | 9908729 | 2/1999 |
| WO | 9916500 | 4/1999 |
| WO | 9925336 | 5/1999 |
| WO | 9929353 | 6/1999 |
| WO | 0032238 | 6/2000 |
| WO | 0032267 | 6/2000 |
| WO | 0045744 | 8/2000 |
| WO | 0149358 | 7/2001 |
| WO | 0160441 | 8/2001 |
| WO | 0238065 | 5/2002 |
| WO | 0243796 | 6/2002 |
| WO | 02076509 | 10/2002 |
| WO | 03022265 | 3/2003 |
| WO | 03026718 | 4/2003 |
| WO | 03059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2006036970 | 4/2006 |
| WO | 2006039237 | 4/2006 |
| WO | 2006102359 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007090382 | 8/2007 |
| WO | 2007090385 | 8/2007 |
| WO | 2007109114 | 9/2007 |
| WO | 2008003298 | 1/2008 |
| WO | 2008014222 | 1/2008 |
| WO | 2008045228 | 4/2008 |
| WO | 2008086794 | 7/2008 |
| WO | 2008089730 | 7/2008 |
| WO | 2008101486 | 8/2008 |
| WO | 2008109114 | 9/2008 |
| WO | 2008125890 | 10/2008 |
| WO | 2008137237 | 11/2008 |
| WO | 2009002855 | 12/2008 |
| WO | 2009014692 | 1/2009 |
| WO | 2009018816 | 2/2009 |
| WO | 2009026914 | 3/2009 |
| WO | 2009036118 | 3/2009 |
| WO | 2009036135 | 3/2009 |
| WO | 2009066330 | 5/2009 |
| WO | 2009096822 | 8/2009 |
| WO | 2009100394 | 8/2009 |
| WO | 2009120361 | 10/2009 |
| WO | 2009121565 | 10/2009 |
| WO | 2009135125 | 11/2009 |
| WO | 2010009335 | 1/2010 |
| WO | 2010021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010146096 | 12/2010 |
| WO | 2010147805 | 12/2010 |
| WO | 2011009096 | 1/2011 |
| WO | 2011028419 | 3/2011 |
| WO | 2011097103 | 8/2011 |

OTHER PUBLICATIONS

International Search Report and Written PCT/US11/50392, mailed Nov. 7, 2011.
Abstract from Liggins, R. T., Hunter, W. L and Burt, H. M. 'Solid-state characterization of paclitaxel.' Journal of Pharmaceutical Sciences, 86: 1458-1463, (1997).
Alexis et al., 'In vitro study of release mechanisms of paclitaxel and rapamycin from drug-incorporated biodegradable stent matrices' Journal of Controlled Release 98 (2004) 67-74.
Buvardi, S., et al., 'Merck Index', 1996, Merck and Co., p. 144.
Charles et al.; 'Ceramide-Coated Balloon Catheters Limit Neointimal Hyperplasia After Stretch Injury in Carotid Arteries' Circ. Res. 2000;87;282-288.
Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.
Cortese et al., "Paclitaxel-coated balloon versus drug-eluting stent during PCI of small coronary vessels, a prospective randomised clinical trial. The PICCOLETO Study", Heart 2010; 96:1291-1296.
Finkelstein et al., "Local Drug Delivery via a Coronary Stent with

(56) References Cited

OTHER PUBLICATIONS

Programmable Release Pharmocokinetics," 2003, Circulation, 107, 777-784.

International Preliminary Report on Patentability of International Application No. PCT/DE20071001173 dated Aug. 4, 2009.

J. Wohrle et al., 'Comparison of the heparin coated vs the uncoated Jostent no influence on restenosis or clinical outcome' European Heart Journal, 2001, vol. 22, pp. 1808-1816.

Mastropaolo et al.; 'Crystal and molecular structure of paclitaxel (taxol)' Proc. Natl. Acad. Sci. USA vol. 92, pp. 6920-6924, Jul. 1995.

Partial European Search Report in EP 07005256.8, dated Jan. 25, 2008.

Presentation by Dr. Cortese, "Paclitaxel-eluting balloon versus paclitaxel-eluting stent in small coronary vessel disease." The Piccoleto Trial.

Scollott, S.J., et al., Taxol Inhibits Neointimal Smooth Muscle Cell Accumulation after Angioplasty in the Rat, 1995, Journal of Clinical Investigation, 95, pp. 1869-1876.

Westedt et al., "Paclitaxel releasing films consisting of poly(vinyl alcohol)-graft-poly(lactideco-glycolide) and their potential as biodegradable stent coatings." 2006, J Control Release 111, 235-46 (abstract).

Written Opinion for PCT/DE2008/000096.

Xu et al., "Lactic-co-glycolic acid polymer with rapamycin coated stent reduces neo-intimal formation in a porcine coronary model", Journal of Clinical Cardiology, 2004, abstract.

Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.

Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.

Axel De Labriolle et al., "Paclitaxel-eluting balloon: From bench to bed", Catheterization and Cardiovascular Interventions, vol. 73. No. 5, Apr. 1, 2009, pp. 643-652.

Cardiovascular and Interventional Radiology, Supplement 1, Sep. 28-Oct. 2, 1997, 158-161.

PCT/US 08/72660 Search Report, Nov. 6, 2008.

PCT/US 2005/47235 Search Report, Dec. 28, 2005.

U.S. Appl. No. 61/322,451, filed Apr. 9, 2010.

U.S. Appl. No. 61/330,201, filed Apr. 30, 2010.

U.S. Appl. No. 61/332,544, filed Apr. 9, 2010.

U.S. Appl. No. 61/352,117, filed Jun. 7, 2010.

U.S. Appl. No. 61/379,608, filed Sep. 2, 2010.

U.S. Appl. No. 61/385,849, filed Sep. 23, 2010.

U.S. Appl. No. 61/394,104, filed Oct. 18, 2010.

U.S. Appl. No. 61/421,054, filed Dec. 8, 2010.

Scheller et al., "Treatment of Coronary In-Stent Restenosis with a Paclitaxel-Coated Balloon Catheter", The New England Journal of Medicine, 2006; 355:2113-24.

Dowding et al., "Preparation and Swelling Properties of Poly(NIPAM) "Minigel" Particles Prepared by Inverse Suspension Polymerization," Journal of Colloid and Interface Science 221, 268-272 (2000).

Panda et al., "Synthesis and swelling characteristics of poly(N-isopropylacrylamide) temperature sensitive hydrogels crosslinked by electron beam irradiation," Radiation Physics and Chemistry 58 (2000) 101-110.

U.S. Appl. No. 61/394,104, filed Oct. 18, 2010; Inventor: Radhakrishnan et al.

Scheller et al., "A further alternative; Balloons can be coated, as well" Newsletter from annual meeting in DGK Apr. 21, 2006.

\* cited by examiner

COATING PROCESS FOR DRUG DELIVERY BALLOONS USING HEAT-INDUCED REWRAP MEMORY

CROSS-REFERENCE TO RELATED APPLICATIONS

This application claims priority to U.S. provisional application 61/379,608, filed Sep. 2, 2010, incorporated herein by reference in its entirety.

BACKGROUND OF THE INVENTION

The invention pertains to catheters and catheter balloons that include drug coatings for delivery to a site within a body passageway.

Sometimes following an initially successful angioplasty or other primary treatment restenosis occurs within weeks or months of the primary procedure. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, the use of drug-eluting stents, use of drug delivery balloons, cutting balloons, cryotherapy systems and the like.

Drug delivery balloons that deliver drug to an internal site upon expansion are known. Some involve perfusion of a drug composition through the balloon wall or from a spongy layer on the balloon wall. Others involve delivery of solid particulate drug, often carried in a polymer or other excipient to the site.

Delivery of drug from the surface during expansion provides benefits of pushing the drug into the specific tissue to be effected and is especially suited for delivering drugs that prevent restenosis during a dilation of a stenotic lesion.

Known drug delivery balloons include paclitaxel coated balloons. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines or onto a folded or unfolded balloon.

Earlier investigations of paclitaxel coated balloons have shown that it is desirable to control the morphology of the drug on the balloon, that with paclitaxel coated balloons paclitaxel dihydrate paclitaxel crystalline form facilitates longer tissue residence time, that the formation of crystalline paclitaxel dihydrate can be controlled by use of vapor annealing of the balloon, and that temperature change at the delivery site can be used to trigger a change in the bonding properties of a drug or drug-containing composition to the balloon.

A variety of techniques have been described for preparing drug coated balloons.

Several balloon coating techniques previously described involve coating a folded and wrapped balloon, by immersion, spraying, pipette, syringe or use of applicator tip such as a wire or capillary that contacts a balloon. In some techniques wicking into the folds is achieved in varying degrees and sometimes residual coating on the outer surface is wiped out. In one technique an applicator is inserted under the fold edge to inject coating solution into the folds. Within the folds the drug coating texture and thickness varies depending on whether the fold is completely filled, and the varied spacing between outer surfaces of the balloon. The result is a coating that is non-uniform and which varies in delivery behavior between its thickest and thinnest portions. If an inflated balloon is coated a more uniform coating is provided. However the balloon must subsequently be folded and wrapped. Folding machinery typically application of heated prongs as the balloon is evacuated or drawing the balloon through a die opening as pressure is withdrawn. Drug coatings for DEB balloons are not practically put through conventional folding machinery. They leave material on the contacting parts of folding machines which interferes with the operation and which also causes reduction of the coat weight uniformity.

There is an ongoing need for improved methods for forming drug delivery balloon catheters that provide durable coatings which can be reliably manufactured.

SUMMARY OF THE INVENTION

The inventive method uses annealed fold/wrap memory induced in a balloon before application of a coating to a balloon surface to overcome the need to use a folding apparatus to fold and wrap a drug coated balloon.

In some aspects the invention pertains to a method of producing a drug coated balloon that comprises the steps of:
subjecting a balloon catheter with a folded and wrapped balloon thereon to a pre-annealing step to induce a fold/wrap memory in the resulting pre-annealed balloon;
unfolding the pre-annealed balloon sufficiently to expose the full circumferential surface of the balloon by application of an inflation pressure that retains said fold/wrap memory;
applying a drug coating formulation to the unfolded balloon surface;
releasing pressure to relax the balloon and induce creasing along fold memory; and
evacuating the balloon slowly to induce refolding and rewrapping of the balloon.

Further aspects of the invention pertain to drug delivery balloon catheters produced using the inventive methods.

In some embodiments a balloon protector is gradually slid over the coated balloon concurrently with the evacuating step to initiate refolding and rewrapping and/or propagate the refolding and rewrapping along the length of the balloon.

In some embodiments the balloon catheter is subjected to a post-annealing step after the drug coating has been applied and the balloon refolded and rewrapped.

These and other aspects and embodiments are described in the detailed description, the drawings and/or the claims which follow.

DETAILED DESCRIPTION OF THE INVENTION

Figure 1:
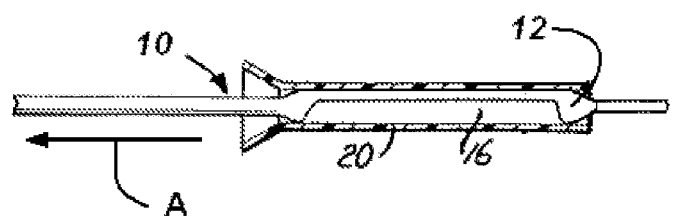
FIG. 1 depicts in cross section a distal end region of a balloon catheter including a drug coated balloon and a balloon protector after the pre-annealing step.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Drug delivery balloon systems are known and have been described in at least the following documents:

U.S. Pat. No. 5,102,402, Dror et al (Medtronic, Inc.);
U.S. Pat. No. 5,370,614, Amundson et al, (Medtronic, Inc.);
WO 9916500, Medtronic,
WO 2009066330, Medtronic
U.S. Pat. No. 5,954,706, Sahatjian (Boston Scientific Corp);
WO 00/32267, SciMed Life Systems; St Elizabeth's Medical Center (Palasis et al);
WO 00/45744, SciMed Life Systems (Yang et al);
R. Charles, et al, "Ceramide-Coated Balloon Catheters Limit Neointimal Hyperplasia After Stretch Injury in Cartoid Arteries," *Circ. Res.* 2000; 87; 282-288;
U.S. Pat. No. 6,306,166, Barry et al, (SciMed Life Systems, Inc.);
US 2004/0073284, Bates et al (Cook, Inc; MED Inst, Inc.);
US 2006/0020243, Speck;
US 2010/0063585 Hemoteq AG, (Hoffman et al);
US 2010/0179475 Hemoteq AG, (Hoffman et al);
US 2008/0118544, Wang;
US 2008/0255509, Wang (Lutonix); and
US 2008/0255510, Wang (Lutonix);
US 2010/0055294, Wang, (Lutonix);
US 2010/076542, Orlowski, (Eurocore);
US 2010/0145266, Orlowski, (Eurocore);

and in the following US patent applications:

Ser. No. 12/765,522 filed Apr. 22, 2010, claiming benefit of U.S. provisional application 61/172,629, filed Apr. 24, 2009, entitled "Use of Drug Polymorphs to Achieve Controlled Drug Delivery From a Coated Medical Device;"
Ser. No. 12/815,138, filed Jun. 14, 2010, claiming benefit of U.S. provisional application 61/224,723, filed Jul. 10, 2009, entitled "Use of Nanocrystals for a Drug Delivery Balloon; 12/815,138, filed Jun. 14, 2010, 61/271,167, filed Jul. 17, 2009, entitled "Nucleation of Drug Delivery Balloons to Provide Improved Crystal Size and Density;" and
U.S. provisional application 61/291,616, filed Dec. 31, 2010, entitled "Cryo Activated Drug Delivery Cutting Balloon."

For purposes of the invention the term drug includes both therapeutic agents and diagnostic agents. Non-limiting examples of drugs that may be employed include anti-restenosis agents, antiproliferative agents, antibiotic agents, antimitotic agents, antiplatelet agents, alkylating agents, platinum coordination complexes, hormones, anticoagulants, fibrinolytic agents, antimigratory agents, antisecretory agents, anti-inflammatory agents, indole acetic acids, indene acetic acids, immunosuppressive agents, angiogenic agents, angiotensen receptor blockers, nitric oxide donors, anti-sense oligonucleotides, cell cycle inhibitors, mTOR inhibitors, growth factor receptor signal inhibitors, transduction kinase inhibitors, retenoids, cyclin/CDK inhibitors, HMG co-enzyme reductase inhibitors, protease inhibitors, viral gene vectors, macrophages, monoclonal antibodies, x-ray contrast agents, MRI contrast agents, ultrasound contrast agents, chromogenic dyes, fluorescent dyes, and luminescent dyes.

In some embodiments the drug is a lipophilic substantially water insoluble drug, such as paclitaxel, rapamycin (also known as sirolimus), everolimus, zotarolimus, biolimus A9, dexamethasone, tranilast or another drug that inhibits restenosis. Other drugs that may be suitable are described in the documents incorporated elsewhere herein. Mixtures of drugs, for instance two or more of paclitaxel, rapamycin, everolimus, zotarolimus, biolimus A9, dexamethasone and/or tranilast may be employed.

Further examples of drugs include estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; a radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a radiolabelled form of any of the foregoing; or a mixture of any of these.

The drug may be one that has polymorph forms, i.e. at least two characterizable morphologies that have different solubilities, or crystal forms. In some embodiments the different morphological forms have characteristics that affect tissue uptake of the drug at the delivery site. Drugs such as paclitaxel have more than one such morphological form. These have different solubilities and dissolution rates in body fluids, including blood. For some embodiments the drug is provided in a specific polymorph form(s) or distribution of such forms to facilitate a particular therapeutic objective.

In exemplary embodiments a drug coating on or in the carrier film comprises dose density of between $0.25/\mu g\ mm^2$ and $5\ \mu g/mm^2$ of a drug, for instance paclitaxel, rapamycin, everolimus, zotarolimus, biolimus A9, dexamethasone and/or tranilast.

In some embodiments of a paclitaxel containing drug coating, the fraction of the paclitaxel in the coating that is amorphous is from 0-25%, for instance about 1% to about 5%, based on total paclitaxel weight. In some embodiments the fraction of the paclitaxel in the coating that is anhydrous from 0% to about 99%, for instance 5-95%, about 10%, about 15%, about 20%, about 25%, about 30%, about 40%, about 50%, about 60%, about 70%, about 70%, or about 80%, based on total paclitaxel weight. In some embodiments the fraction the paclitaxel in the coating that is dihydrate crystalline is from 1% to 100%, for instance 1-99%, 5-95%, about 10%, about 15%, about 20%, about 25%, about 30%, about 35%, about 40%, about 45%, about 50%, about 55%, about 60%, about 65%, about 70%, about 75%, about 80%, about 85%, about 88%, about 89%, about 90%, about 91%, about 92%, about 93%, about 94%, about 95%, about 96%, about 97%, about 98%, or about 99%, based on total paclitaxel weight.

In some embodiments the drug may be a solid crystalline form that includes organic solvent molecules such as dimethylsulfoxide (DMSO), N,N'-dimethylformamide (DMF), N,N'-dimethylacetamide (DMAC), N-methyl-2-pyrrolidone (NMPO), 1,3-dimethyl-2-imidazolidinone (DMEU), 1,3-dimethyl-3,4,5,6-tetrahydro-2-(1H)-pyrimidinone (DMPU), and acetonitrile and mixtures thereof, with or without water molecules in the crystal structure. Examples of such crystalline forms include the paclitaxel solvates described in U.S. Pat. No. 6,858,644.

The balloons, may be elastic and/or inelastic balloons, and may be formed of material such as polyamides (for example, nylon 12 or DURETHAN® available from Bayer or CRISTAMID® available from Elf Atochem), polyethylene terephathalate (PET), polyurethane, latex, silicone, polyethylene (PE) (for example, Marlex® high-density polyethylene, Marlex® low-density polyethylene, and a linear low density polyethylene such as REXELL®), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester (for example, a polyether-block-ester elastomer such as ARNITEL® available from DSM Engineering Plastics or a polyester elastomer such as HYTREL® available from DuPont), polyvinylchloride (PVC), polyether-block-amide (PEBA, for example, available under the trade name PEBAX®), polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like.

In some embodiments the balloon wall is formed of one or more layers of Pebax® polymers, suitably Pebax® 6333, Pebax® 7033, Pebax® 7233; nylon polymers, for instance nylon 11 or nylon 12; PET; polyester elastomer, such as Hytrel® or Arnitel® resins having a Shore D Hardness of about 60 or more, or a mixture thereof. In some embodiments the balloon may be formed of two or more layers, for instance a layer of nylon 12 and a layer of Pebax® 6333, Pebax® 7033, Pebax® 7233; or two or more alternating layers of a relatively inelastic polymer such as PET or nylon 12 alternating with two or more layers or more layers of a thermoplastic elastomer such as Pebax® 5533 Pebax® 6333, Pebax® 7033, Pebax® 7233 or a Hytrel® or Arnitel® having a Shore D Hardness of about 50 or more.

The balloon will typically have a length of at least 1 cm, preferably being in a range from about 1.0 cm to 25 cm, and may have diameters in a range from 1.5 mm to about 20 mm, for instance 1.5 to 5 mm.

In known processes for producing balloon catheters with uncoated balloons, a balloon protector can be slid over the balloon after it has been wrapped and before it is sterilized. The balloon protector, typically a sleeve with a flared distal end or with flared proximal and distal ends slides freely over the catheter and over the wrapped balloon. The catheter, with balloon protector in place, can be subjected to heat annealing, typically at a temperature between the temperature at which the balloon will be sterilized and the temperature at which the balloon was molded. The balloon catheter is then packaged and sterilized. The annealing step provides a relatively weak fold/wrap memory that survives sterilization and facilitates maintenance of the balloon in a tightly wrapped configuration after the balloon protector is removed to keep a low profile during delivery. At the time of use the balloon protector slid distally off the catheter and discarded before insertion of the catheter into a body passage way.

The invention utilizes a pre-annealing step, performed before coating the balloon. The pre-annealing may be substantially the same as is currently used for uncoated balloons. It is performed with the balloon protector in place, the temperature is above room temperature and below the temperature at which the balloon is blown. Typically some balloon shrinkage will occur in the course of this pre-annealing step, and so the dimension change should be designed into the balloon component. Exemplary annealing treatment temperatures are in the range of about 35° C. to about 85° C., about 35° C. to about 70° C., about 35° C., about 45° C., about 55° C., about 65° C., or about 70° C. The annealing time may be about 3 minutes to about 2 hours for instance about 5 min. to about 15 min. at 70° C. or about 5 minutes to about 30 minutes at 40° C. A convection oven may be used to facilitate rapid equilibration of the catheter at the treatment temperature.

The mass of the balloon can affect the time needed to a balloon is pre-annealed at a given temperature. For instance 7 mm dia.×40 mm long balloons of Pebax® 7033 or Pebax® 7233 can be pre-annealed at 70° C. for 5 min whereas larger mass balloons may take a longer time, e.g. 10 minutes, for a 7 mm dia.×100 mm long balloon of the same material. Pre-annealing times may be longer at lower temperatures. The choice of balloon material may also affect the time and temperature of the pre-annealing step.

Balloons may be initially folded by any known process and apparatus, including without limitation the processes of U.S. Pat. No. 4,681,092, U.S. Pat. No. 5,087,246, U.S. Pat. No. 5,147,302, U.S. Pat. No. 5,350,361, U.S. Pat. No. 6,283,743.

The balloon protector is suitably one that can be slid proximally along the catheter after wrapping. Suitably it is designed to exert some compressive force to the wrapped balloon but has a lubricated or lubricious inner surface and sufficient resiliency to allow it to be slid on and off the balloon readily. In some embodiments the balloon protector is formed of an crosslinked elastomeric silicone rubber. In some embodiments the balloon protector is lubricated with a silicone oil or fluoropolymer lubricant. In alternative embodiments the balloon protector may have a fluoropolymer inner surface configured for instance with a longitudinal slit, and an outer region of an elastomeric polymer such as a silicone rubber. Exemplary balloon protector configurations include for instance those disclosed in U.S. Pat. No. 4,930,341, U.S. Pat. No. 5,015,231, U.S. Pat. No. 5,352,236, U.S. Pat. No. 6,152,944, U.S. Pat. No. 6,100,146.

In some embodiments if the balloon can maintain a wrapped profile reliably during pre-annealing without assistance, the use of a balloon protector in the pre-annealing step may not be required.

The number of balloon pleats is not critical to the invention. In general three or more will be used. For larger balloons a larger number of pleats may provide a better tracking profile. For instance balloons of about 5 mm or more may have a better tracking profile with 4, 5, 6, or more pleats. For instance a 7 mm balloon may employ a 5-pleat wrapped configuration.

After the balloon catheter assembly has been pre-annealed and returned to ambient temperature the balloon protector is slid off the balloon. In at least some embodiments the balloon protector is moved proximally along the catheter outer shaft until the balloon has been fully exposed. This can be done manually or automatically, for instance with a robotic apparatus that separately engages the catheter shaft and the balloon protector and then relatively moves the protector along the catheter axis.

Once the annealed balloon is exposed the pressure is applied to the balloon interior sufficient to at least partially inflate the balloon. The applied pressure should be sufficient to unfold the balloon to expose the full circumferential surface of the balloon, but not high enough that the fold/wrap memory is destroyed by the inflation pressure or by the combination of inflation pressure and coating solvent treatment. In at least some embodiments the inflation pressure is from about 0.25 to about 3 atm, for instance about 0.5 to about 2 atm, above ambient. The balloon should be generally cylindrical but some creasing may be tolerable so long as the coating method chosen apply the coating formulation substantially uniformly over the surface area to be coated.

The coating is then applied by any suitable means, for instance by spray, brush, pipette, capillary, wire, syringe, roller or the like. In some embodiments a micropipette or microsyringe applicator is used that moves longitudinally along the balloon as the balloon catheter is rotated. In some embodiments the applicator provides a fixed amount of coating solution to the balloon surface. The rate of application in some embodiments is set to minimize or eliminate loss of coating off the balloon. In some embodiments a region below the balloon may be monitored with a photodetector that is capable of monitoring coating material escaping from the balloon.

The coating composition comprises at least a drug as described above and a solvent. In some embodiments the coating composition may also include a degradable polymer or excipient. Examples of solvent can include, but are not limited to, DMSO, DMF, DMAC, NMPO, DMEU, DMPU, methanol, ethanol, 1-propanol, isopropanol, acetone, methyl ethyl ketone, tetrahydrofuran, diethyl ether, cyclohexanone, acetonitrile, methyl acetate, ethyl acetate, toluene, xylene, and mixtures thereof. In some embodiments water may be a suitable solvent for the coating composition. The coating solution may be provided by mixing stock solutions of the drug and excipient at the time use.

As examples of excipient or polymer materials that may also be included in a drug coating solution, any of the materials previously described in any of U.S. Pat. No. 6,306,166, Barry et al, (SciMed Life Systems, Inc.); US 2004/0073284, Bates et al (Cook, Inc; MED Inst, Inc.); US 2006/0020243, Speck; WO 2008/003298 Hemoteq AG, (Hoffman et al); WO 2008/086794 Hemoteq AG, (Hoffman et al); US 2008/0118544, Wang; US 2008/0255509, Wang (Lutonix); and US 2008/0255510, Wang (Lutonix); US 2010/0055294, Wang, (Lutonix); US 2010/076542, Orlowski, (Eurocore); US 2010/0145266, Orlowski, (Eurocore), may be used. Examples of excipients that may be employed include contrast agents, various surfactants, oils, fats, sugars such as mannitol, contrast agents such as iopromide, citrate esters such as acetyltributyl citrate, acetyl triethyl citrate, tributyl citrate, triethyl citrate, glycerol esters of short chain (i.e. $C_2$-$C_8$) mono-carboxylic acids such as triacetin, ascorbate esters, polyvinyl pyrrolidone (PVP), lactic acid polymers and lactate copolymers, such as PLGA.

A particular exemplary embodiment uses a mixture of paclitaxel and acetyltributyl citrate (ATBC) in acetone solution at a weight ratio of paclitaxel to ATBC in the range of about 90/10 to about 25/75, for instance 60/40 or 50/50.

In the case of a hydrophobic drug, the solvent can be one in which water is miscible or has a high solubility. In those case water may be separately applied to the balloon before, concurrent with, or after the drug solution is applied, in order to facilitate deposition of the drug onto the balloon substrate. Provision of water in this way can drive precipitation of the drug or drug/excipient mixture from solution. Water may also be added to the coating composition in an amount that does not induce precipitation of the drug and excipients, if present, but that places the composition near saturation, suitably using a lower boiling solvent. As the coated balloon rotates the lower boiling solvent flashes off, inducing the applied coating solution to surpass saturation and initiate precipitation of the drug/excipient coating.

The solution composition may also be manipulated to provide a desired drug morphology. In the case of paclitaxel for instance, addition of water to a paclitaxel-containing solution as it is being applied or by pre-spray or post-spraying can both facilitate precipitation of the drug from solution and also induce the formation of the paclitaxel dihydrate crystal form. Crystalline dihydrate generally provides a longer residence time at the treatment site and so is generally the preferred form for delivery from a drug delivery balloon. In some embodiments a balloon may be sprayed with water and then have a fixed amount of a solution comprising paclitaxel at a predetermined concentration in a water miscible solvent such as acetone, tetrahydrofuran, ethanol, DMSO, DMF, DMAC, or acetonitrile, applied by micropipette or microsyringe to give a coating comprising crystalline paclitaxel dihydrate. In other embodiments a solution comprising paclitaxel at a predetermined concentration in a water miscible solvent, is mixed with an amount of water that does not cause precipitation of the paclitaxel and any excipient present. The mixed solution is then applied to a balloon and the balloon rotated for a time after application. The solvent flashes off producing a coating comprising dihydrate crystalline paclitaxel.

The balloon catheter may be rotated as the coating material is applied and as long thereafter as is needed to assure the coating won't drip from the balloon or migrate by gravity.

In some embodiments the coating may be overcoated with a degradable polymer or undercoated with a material that facilitates release upon balloon expansion. Any material previously described for such purpose may be used.

After the desired amount of coating material has been applied, including any undercoatings and overcoatings, the balloon pressure is released allowing the balloon to relax to a semi-pleated state. The fold/wrap memory induced in the first annealing step will initiate pleating along the remembered lines.

Then a balloon protector may be gradually slid over the balloon while slowly evacuating the internal pressure in the balloon. In embodiments where a balloon protector used in the pre-annealing step has been moved proximal of the balloon during the coating the same balloon protector is moved proximally in this step. If a balloon protector used in the pre-annealing step has been entirely removed from the balloon catheter assembly, the balloon protector that is used may be the same or a different protector.

Referring now to the Figures there is shown the distal portion 10 of a medical catheter. Catheter distal portion 10 includes a balloon 12 having pleats 16. In FIG. 1 the balloon is shown with a balloon protector 20 over the pleats 16. After the pre-annealing step the balloon protector 20 is moved in the direction shown by arrow A and the balloon is unfolded for coating and refolding/pleating in accordance with the invention.

Figure 2:
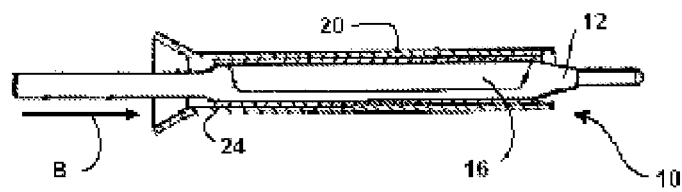
FIG. 2 is a similar view to FIG. 1 after the balloon has been coated and refolded and rewrapped in accordance with the invention.

FIG. 2 is a view as in FIG. 1, but after the balloon has been refolded and rewrapped and the balloon protector has been replaced by sliding in the direction of arrow B. The balloon includes a uniform coating 22 comprising a drug such as paclitaxel, optionally with an excipient such as acetyltributyl citrate.

Gradually sliding the balloon protector over the coated and relaxed balloon allows the creases induced by the fold/wrap memory to propagate along the remembered wrap configuration so that the balloon substantially rewraps as the protector moves over the balloon without the need to run the coated balloon through a wrapping apparatus. Exemplary times for reapplying the balloon protector may be from about 5 seconds to about 2 minutes. For instance for a 7 mm diameter balloon of 100 mm in length, a suitable time for reapplying the balloon protector is about 15 to 20 seconds.

The coating may still have some residual solvent and/or water present at the time of reapplying the balloon protector. In this sense the coating may be taken as "wet," i.e. not be fully dry-to-the-touch. Evacuation and sliding of the balloon protector typically may be started once the balloon has sufficiently relaxed to form creases. In some embodiments the balloon protector can be applied immediately after application of the coating solution. In some embodiments, however the time between coating application and reapplication of the balloon protector may be enough to produce a dry-to-the-touch coating.

In some alternate embodiments gradual evacuation of the balloon alone may be sufficient to propagate the creases induced by the fold memory and rewrap of the balloon. In those cases a stent may optionally be crimped over the rewrapped balloon.

In at least some embodiments the coated balloon/catheter/protector assembly, or balloon/catheter/stent assembly is subjected to a second annealing. The second annealing conditions can substantially duplicate those of the first annealing step or they may be at a different temperature and/or for a different time provided that the same conditions on the temperature range employed apply. This assures that the balloon will maintain wrapped profile when the protector is removed and that any residual solvent has been removed before sterilization. In some embodiments this reannealing step may not be necessary, especially if the assembly is given a rest period in a clean room for an extended time, or if the sterilization conditions themselves are at a high enough temperature to provide a wrap memory, e.g. at a temperature of at least about 50° C.

The coated balloon provides a substantially uniform coating which has superior durably on the balloon compared to fold-filled coatings, while still providing good release into tissue at the treatment site.

In embodiments where the drug-containing layer is overcoated with a protective polymeric layer, the layer may be one that that substantially disintegrates in the course of the deployment or during transfer of the drug from the device at the site of administration. Suitably such protective layer has a thickness of 0.5 µm or less, 0.1 µm or less, or 0.01 µm or less. Polymers or copolymers that have a good solubility in water and a molecular weight sufficient to slow dissolution of the coating enough to provide practical protection may be used. Other protective layers may be effective if they break up into fine particles during drug delivery, for instance upon balloon expansion. Protective coating thickness may be adjusted to give an acceptable dissolution and/or degradation profile. Ionically crosslinked polysaccharides, such as calcium alginate may be used as a protective layer or as an excipient for the drug.

In embodiments where the drug containing layer is applied over an underlayer, the underlayer material may be one that has a high solubility in bodily fluids to undercut the drug facilitate breakup of the drug-containing layer upon balloon expansion. An example of a suitable underlayer material is pectin.

The devices of the present invention, may be deployed in vascular passageways, including veins and arteries, for instance coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of producing a drug coated balloon that comprises the steps of:
   subjecting a balloon catheter with a folded and wrapped balloon thereon to a pre-annealing step to induce a fold/wrap memory in the resulting pre-annealed balloon;
   unfolding the pre-annealed balloon sufficiently to expose the full circumferential surface of the balloon by application of an inflation pressure that retains said fold/wrap memory;
   applying a drug coating formulation to the unfolded balloon surface, the drug coating formulation comprising a drug, a solvent and optionally water;
   releasing pressure to relax the balloon and induce creasing along fold memory; and
   evacuating the balloon slowly to induce refolding and rewrapping of the balloon,
   wherein in said step of evacuating the balloon slowly, a balloon protector is concurrently gradually slid over the coated balloon and wherein an elapsed time between the step of applying the drug formulation and beginning to slide the balloon protector over the balloon is less than that needed to fully remove all solvent and/or water in the coating.

2. A method as in claim 1 wherein the balloon is subjected to an inflation pressure of from about 0.5 to about 3 atm in said unfolding step.

3. A method as in claim 1 wherein the balloon catheter is subjected to a post-annealing step after the drug coating has been applied and the balloon refolded and rewrapped.

4. A method as in claim 1 wherein the coating comprises at least one drug selected from the group consisting of paclitaxel, rapamycin, everolimus, zotarolimus, biolimus A9, dexamethasone, tranilast, and another drug that inhibits restenosis.

5. A method as in claim 1 wherein the coating further comprises an excipient.

6. A method as in claim 5 wherein said excipient is a member of the group consisting of contrast agents, surfactants, oils, fats, sugars, citrate esters, glycerol esters of $C_2$-$C_8$ mono-carboxylic acids, ascorbate esters, polyvinyl pyrrolidone (PVP), lactic acid polymers and copolymers.

7. A method as in claim 1 wherein the drug comprises paclitaxel and the coating further comprises acetyltributyl citrate (ATBC) at a weight ratio of paclitaxel to ATBC in the range of about 90/10 to about 25/75.

8. A method as in claim 1 wherein the step of applying a drug coating formulation to the unfolded balloon surface comprises applying a composition of a drug in a solvent solution.

9. A method as in claim 8 wherein the solvent is water miscible and water is added to the solvent solution at the time of application.

10. A method as in claim 9 wherein the drug is paclitaxel and the solvent is acetone.

11. A method as in claim 1 further comprising crimping a stent over the rewrapped balloon.

12. A method as in claim 1 wherein the coating comprises two or more members of the group consisting of paclitaxel, rapamycin, everolimus, zotarolimus, biolimus A9, dexamethasone and tranilast.

13. A method as in claim 1 wherein the balloon is formed at a blowing temperature and the pre-annealing step is conducted at a pre-anneal temperature that is above room temperature and below the temperature at which the balloon is blown.

14. A method as in claim 12 wherein the pre-anneal temperature is from about 35° C. to about 70° C.

15. A method of producing a drug coated balloon that comprises the steps of:

subjecting a balloon catheter with a folded and wrapped balloon thereon to a pre-annealing step to induce a fold/wrap memory in the resulting pre-annealed balloon;

unfolding the pre-annealed balloon sufficiently to expose the full circumferential surface of the balloon by application of an inflation pressure that retains said fold/wrap memory;

applying a drug coating formulation to the unfolded balloon surface;

releasing pressure to relax the balloon and induce creasing along fold memory; and evacuating the balloon slowly to induce refolding and rewrapping of the balloon, wherein in said step of evacuating the balloon slowly, a balloon protector is concurrently gradually slid over the coated balloon, and wherein the coating is not fully dry to the touch when the balloon protector is slid over the coated balloon.

* * * * *